US008846722B2

(12) United States Patent
Ecker et al.

(10) Patent No.: US 8,846,722 B2
(45) Date of Patent: Sep. 30, 2014

(54) ANIMAL PARASITE-CONTROL METHOD USING INSECT GROWTH REGULATORS

(75) Inventors: William Ecker, Secaucus, NJ (US); Lance Hemsarth, Secaucus, NJ (US)

(73) Assignee: The Hartz Mountain Corporation, Secaucus, NJ (US)

(*) Notice: Subject to any disclaimer, the term of this patent is extended or adjusted under 35 U.S.C. 154(b) by 225 days.

(21) Appl. No.: 13/530,990

(22) Filed: Jun. 22, 2012

(65) Prior Publication Data

US 2012/0264788 A1    Oct. 18, 2012

Related U.S. Application Data

(63) Continuation of application No. 12/206,648, filed on Sep. 8, 2008.

(60) Provisional application No. 60/970,444, filed on Sep. 6, 2007, provisional application No. 60/970,621, filed on Sep. 7, 2007.

(51) Int. Cl.
| | |
|---|---|
| *A61K 31/44* | (2006.01) |
| *A61K 31/09* | (2006.01) |
| *A01N 49/00* | (2006.01) |
| *A61K 31/415* | (2006.01) |
| *A61K 31/4402* | (2006.01) |
| *A61K 31/216* | (2006.01) |
| *A61K 31/231* | (2006.01) |
| *A01N 43/40* | (2006.01) |

(52) U.S. Cl.
CPC ............. *A61K 31/4402* (2013.01); *A61K 31/09* (2013.01); *A01N 49/00* (2013.01); *A61K 31/415* (2013.01); *A61K 31/216* (2013.01); *A61K 31/231* (2013.01); *A01N 43/40* (2013.01)
USPC ........................................................ 514/345

(58) Field of Classification Search
CPC ... A01N 43/40; A61K 31/216; A61K 31/231; A61K 31/4402
USPC ........................................................ 514/345
See application file for complete search history.

(56) References Cited

U.S. PATENT DOCUMENTS

| | | | |
|---|---|---|---|
| 4,166,107 A * | 8/1979 | Miller et al. ................ | 424/405 |
| 4,439,415 A | 3/1984 | Hennart et al. | |
| 5,567,429 A | 10/1996 | Senbo | |
| 5,632,999 A | 5/1997 | Miller | |
| 6,093,415 A | 7/2000 | Karr et al. | |
| 6,867,223 B2 | 3/2005 | Cottrell et al. | |
| 2007/0020304 A1* | 1/2007 | Tamarkin et al. ........... | 424/405 |

FOREIGN PATENT DOCUMENTS

| | | |
|---|---|---|
| CA | 2221418 | 11/2008 |
| EP | 0714601 A1 | 6/1996 |
| EP | 0979606 A1 | 2/2000 |
| EP | 0714601 A1 | 8/2000 |
| GB | 2396557 * | 6/2004 |
| JP | 04-120002 A | 4/1992 |
| JP | 08-208408 A | 8/1996 |
| JP | 11-060413 A | 3/1999 |
| JP | 2000-109403 A | 4/2000 |
| JP | 2003-026603 A | 1/2003 |
| WO | 93/00809 A1 | 1/1993 |
| WO | 03/051116 A1 | 6/2003 |
| WO | 2006/107905 A1 | 10/2006 |
| WO | 2007/041127 A1 | 4/2007 |

OTHER PUBLICATIONS

Database Biosis (Online), Biosciences Information Service, Philadelphia, PA, US; 1992, Atkinson, T.H. et al: "Volatile Effects of Insect Growth Regulators Against the German Cockroach Dictyoptera Blattellidae", XP002689415, Database accession No. PREV199294038163 *abstract* & Journal of Medicine Entomology, vol. 29, No. 2, 1992, pp. 364-367, ISSN:0022-2585.
Extended European Search Report issued on Jan. 10, 2013 for European Patent Appln. No. 08829454.1.
Office Action issued on Mar. 5, 2013 in corresponding Japanese Patent Appln. No. 2010-524227, filed on Sep. 8, 2008, with English Summary of "Notice of Reasons for Rejection."
International Search Report and Written Opinion of the International Searching Authority (US) for International Application No. PCT/US2008/075628 dated Dec. 3, 2008.
European Patent Office Examination Report of corresponding EP Application No. 08 829 454.4, Apr. 11, 2014.
Canadian Patent Office Examination Report of corresponding CA Application No. 2,698,528, Sep. 26, 2011.
Russian Patent Office Official Action for corresponding RU Application No. 2010113006, Jul. 9, 2012.
Chinese Patent Office First Office Action for corresponding CN Application No. 200880105942.9, May 25, 2012.
Chinese Patent Office Second Office Action for corresponding CN Application No. 200880105942.9, Apr. 11, 2013.
Chinese Patent Office Third Office Action for corresponding CN Application No. 200880105942.9, Nov. 15, 2013.
Chinese Patent Office Fourth Office Action for corresponding CN Application No. 200880105942.9, Apr. 16, 2014.

* cited by examiner

*Primary Examiner* — Aradhana Sasan
(74) *Attorney, Agent, or Firm* — Gottlieb, Rackman & Reisman, PC

(57) ABSTRACT

Methods and formulations for treating animal ectoparasites, effective against parasites such as fleas and ticks are provided. The methods comprise topically co-administering a non-mobile insect growth regulator and a mobile insect growth regulator to the animal. Parasiticidal formulations for treating animal ectoparasites are also provided, which can be safe to use and avoid the many common deleterious side effects of conventional topical formulations. The topical formulations comprise a combination of two insect growth regulators, a non-mobile insect growth regulator and a mobile insect growth regulator. The topical formulation can be packaged with the two insect growth regulators together or packaged to prevent mixing of the two insect growth regulators prior to administering the topical insecticide formulation to the animal.

13 Claims, No Drawings

ANIMAL PARASITE-CONTROL METHOD USING INSECT GROWTH REGULATORS

This application is a continuation of U.S. patent application Ser. No. 12/206,648, filed Sep. 8, 2008, currently pending, which claims the benefit of U.S. Provisional Application No. 60/970,444, filed Sep. 6, 2007, and U.S. Provisional Application No. 60/970,621, filed Sep. 7, 2007, the contents of which are incorporated herein by reference.

BACKGROUND OF INVENTION

This invention relates generally to a method of controlling parasites and formulating and applying topical formulations that can have significant parasiticidal or anti-parasite activity, such as one suitable to use on house pets such as dogs and cats.

The infestation of companion animals with fleas, ticks, and the like is highly undesirable and as such, it is beneficial to develop improved products to fight such infestation. Topical applications can be desirable since many formulations are acceptably safe when used topically, even if not when used internally.

Topical applications are more advantageous if the amount of liquid applied to the animal can be minimized. This should be balanced with the need for appropriate dosage to achieve the desired pesticidal effect. Therefore, it is desirable to use highly active insecticide so that the total volume of the insecticide applied to the animal can be minimized.

Topical applications often contain an insect growth regulator (IGR) component. IGRs kill flea larvae and prevent flea eggs from hatching. Such formulations provide for an effective flea control system since only about 5% of the existing fleas on an animal can be adults and the other 95% in a juvenile state (eggs and larvae). For example, methoprene, hydroprene and pyriproxyfen (commercially available as Nylar) are IGRs that prevent flea eggs from hatching.

However, it has been determined that various IGR containing formulations have drawbacks due the characteristics of the chosen IGR. For some IGRs, it is difficult to maintain an effective concentration at the affected area of the animal and requires that a large volume to be applied. For other IGRs, it is difficult to provide sufficient coverage surrounding the treatment area, thereby permitting parasites to persist in other areas of the animal or in the environment such as pet bedding, carpeting, upholstery, and so forth. Again, a large volume is required to provide coverage.

This can cause considerable mess and can lead to an unpleasant smell. Additionally, if the dosage of a topical formulation is in a large volume, it can be easily shaken off by the animal thereby reducing the effectiveness of the formulation. Furthermore, when the animal is a house pet, there is a further complication in that the formulation should be safe for human contact. A large dose of an IGR may lead to staining of furniture, carpeting and the like. Finally, even if safe, topical formulations should not be irritating or lead to rashes, hair loss or exhibit other unpleasant side effects.

Accordingly, it is desirable to develop improved formulations.

SUMMARY OF THE INVENTION

Generally speaking, in accordance with the invention, a topical application of two IGRs is provided. It has been determined that the topical application of two IGRs—preferably an IGR with high mobility property such as methoprene or hydroprene due to its volatility (mobile IGR) and a non-mobile IGR such as pyriproxyfen—on the same animal, especially a non-human animal, so as to be present at the same time, achieves surprising synergistic effect and offers a broader and more effective means of infestation control than using the same total quantity of either IGR separately.

As referred to herein, a mobile IGR is an IGR that exists in liquid form or as a sublimating solid at room temperature under one atmospheric pressure, which is capable of translocation (vaporizing and redepositing from one area to another area). Examples of a mobile IGR include methoprene and hydroprene. A mobile IGR is volatile and capable of translocation from one area of the animal to another area of the animal or an area in the environment. As referred to herein, a non-mobile IGR is an IGR that exists in solid form without sublimation at room temperature under one atmospheric pressure, which is not capable of translocation. An example of a non-mobile IGR is pyriproxyfen. A non-mobile IGR does not spread or migrate and therefore is capable of maintaining a high effective concentration at the location it is applied.

Due to its increased potency, the application in accordance with the invention requires less total active ingredients. It can be safe to use and avoids many common deleterious side effects of conventional topical application.

One preferred embodiment of the invention provides a topical formulation that contains a combination of either methoprene or hydroprene with pyriproxyfen and at least one additional insecticide capable of providing insecticidal activity on the adult insect ("adulticide"). The selection of the combination of insecticides and insect growth regulators produces a composition having high parasitical activity, thereby providing broad protection against a variety of parasites with a single application of the topical formulation. The use of two selected IGRs has also been determined to lead to a synergistic effect, such as improved activity per total volume ratios. The treatment method using such a formulation can also be useful to improve the speed of result and decrease the reoccurrence, compared to other formulations.

As used herein, the identification of an active ingredient, e.g., pyriproxyfen, is intended to also refer to other pharmaceutically active forms of the active ingredient, such as esters, salts, hydrochlorides, acid or base forms, isomers and so forth.

Thus, an advantage of the invention is to provide a topical application method for controlling parasites.

Another advantage of the invention is to provide an improved method of parasite control application more rapidly and/or more permanently than other topical formulations.

Another advantage of the invention is to provide an improved method of parasite control application using less active ingredients than other topical formulations.

Other objects, advantages and features will be in part apparent and in part pointed out.

DETAILED DESCRIPTION OF THE PREFERRED EMBODIMENTS

In accordance with one preferred embodiment of the invention, a method of animal parasite control is provided which involves a combination of methoprene (or hydroprene), pyriproxyfen and an adulticide that is effective against parasites such as fleas, flea eggs, and other potential targets. This combination of active ingredients can produce a topical formulation that provides broad protection against parasites.

Preferably, the treatment of different parasites can be targeted by including a particular adulticide including, but not limited to, macrocyclic lactones, natural pyrethrins, synthetic pyrethroids, Etofenprox, neo-nicotinoids, phenylpyrazoles, or combinations thereof. The adulticide or combination of adulticides should be present in an amount effective to control parasites in the adult state, preferably between 1% and 90% of the total administration.

The IGRs should be present in an amount effective to control parasites in the juvenile state. The amount of pyriproxyfen is preferably between 0.005% and 5% of the total administration. The amount of methoprene (or hydroprene) is preferably between 0.01% and 10% of the total administration. In a preferred embodiment of the invention, the ratio of methoprene to pyriproxyfen is in the range of 20:1 to 1:20 by weight.

It should be understood that the application of methoprene (or hydroprene), pyriproxyfen and an adulticide can be, without limit to any specific ordering of the application. Thus, it is possible to apply methoprene (or hydroprene), pyriproxyfen, and the adulticide in a single combined formulation or in succession and achieve desirable benefits.

In one preferred embodiment of the invention, the insecticide composition of the invention can be packaged in a single dose package. Single dose containers make storage, use, and disposal more convenient for animal owners.

In another preferred embodiment of the invention, the two IGRs and the adulticide can be packaged in a container having two associated, preferably attached, but individual, separated chambers to prevent the mixing of these ingredients prior to the administration to reduce cross-reactivity and improve the shelf-life and efficacy of a formulation where the adulticide needs to be separated from methoprene and pyriproxyfen. Prior to administration, the packages containing the first and second formulations in their respective separate chambers are opened, and the first and second formulations are dispensed simultaneously or at least at about the same time to the animal.

In another preferred embodiment of the invention, the IGRs and the adulticide is applied to the surrounding of the animal, such as a pet bed or a carpet.

In another preferred embodiment of the invention, the IGRs and the adulticide is prepared in liquid form with a carrier including 1% to 70% aerosol propellants.

In another preferred embodiment of the invention, the IGRs and the adulticide is prepared in liquid form to be dispensed to surfaces via pump spray.

It is understood that the active ingredients need not be mixed together prior to administration of the topical formulation to the animal, but may be stored in suitable carriers separately. Suitable carriers for the IGRs and the adulticide include, but are not limited to, vegetable oils, surfactants, glycols, esters, light petroleum, aldehydes, lactones, triglycerides, amides, silicone polyether copolymers, dialkyl fatty acid amides, pyrrolidones, aqueous dispersions, water, and combinations thereof. The carrier is preferably N,N dialkyl fatty acid amide, and most preferably N,N dimethyl octanamide. The carriers should be present between 1% to 99% of the total weight of the composition.

Because compositions in accordance with preferred embodiments of the invention can be formulated with a relatively high concentration of active ingredients, a relatively small application of a spot or line on the animal can effectively prevent and control parasite infestation on the animal for approximately one, two and even four or more weeks post-administration.

In the preparation of a formulation for use on animals, there are several parameters that should be considered. These are:
(a) Concentration high enough to minimize the volume of the topical applied to the animal (one would not want to put 20 ml, e.g., onto a small dog).
(b) Concentration low enough to achieve effective translocation of the topical insecticide over the animal's skin.
(c) The formulation should be stable for six months at 40° F. and 75% relative humidity, room temperature and −10° F. This helps ensure that the formulation remains stable under the conditions that it could meet in commerce.
(d) Safe to use on the intended animal—particularly non-irritating to at least the intended animal, since the product is applied to the skin. Also safe if ingested by the animal; ingestion can occur when pets groom themselves.
(e) Safe to use by the consumer.
(f) Efficacious in use—should kill greater than 90% of the fleas and ticks up to 28 days.
(g) Efficacy would be reduced if crystallization occurred in the package.
(h) Needs to be aesthetically pleasing—"no oily drop" on the animal when applied.
(i) Fast drying to reduce the chance of the animal shaking off the liquid thereby reducing efficacy.
(j) Microbiologically stable.

The proposed mechanism of synergy is not to be construed as limiting in any way. However, it is believed that methoprene and hydroprene are volatile, with high mobility and therefore capable of migrating throughout an infested area. It is believed that pyriproxyfen possesses long-term chemical stability and potency. Thus, a combination of the migratory property of a mobile IGR such as methoprene or hydroprene with the efficacy of pyriproxyfen achieves increased parasiticidal activity multiplicatively, rather than offering mere additive results.

It can be advantageous to co-administer additional components to increase the efficacy and to reduce the irritation of insecticides to the skin of animals. The formulation can advantageously contain spreading agents such as n-octyl pyrrolidone and dioctylsulfosuccinimide, fragrances, and/or antioxidants. Other additives to the insecticidal composition include but are not limited to fragrances, surfactants and spreading agents to increase performance such as polyoxyethylene (20) sorbitan monolaurate (commercially available as polysorbate 20 or Tween® 20) and polyoxyethylene (20) sorbitan monooleate (commercially available as polysorbate 80 or Tween® 80), and isopropyl myristate. Polymers such as agar, gelatin, alginate, and cationic polymers such as cationic guar, cationic cellulose, cationic acrylates, and polyoxymethylene urea may also be added to provide enrobing of the insecticide to improve safety and adhesion to skin and hair.

In practice, an effective amount of the insecticidal compositions as described herein may be applied to a companion animal, preferably a dog or a cat, as a foaming shampoo, dip, aerosol spray, pump spray, powder, lotion, emulsifiable concentrate, aqueous or liquid flowable, slow release collar, suspension concentrate, powder, and by any other methods suitable for administering topical compositions to animals.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

The following examples of formulations containing two IGRs and one adulticide active ingredients are given for purposes of illustration only and are not intended to be construed in a limiting manner.

Example 1

A Formulation I consistent with an embodiment of the invention is prepared by mixing 0.1% pyriproxyfen, 3.0% methoprene or hydroprene, 40% Etofenprox and 56.9% diisopropyl adipate (DIPA) carrier by weight.

Example 2

A Formulation II consistent with an embodiment of the invention is prepared by mixing 0.05% pyriproxyfen, 10.0% methoprene or hydroprene, 85% phenothrin and 4.95% DIPA carrier by weight.

Example 3

A Formulation III consistent with an embodiment of the invention is prepared by mixing 5.0% pyriproxyfen, 0.1% methoprene or hydroprene, 10% fipronil and 84.9% DIPA carrier by weight.

While there have been shown, described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall therebetween.

What is claimed is:

1. A method of treating parasitic infestation in a non-human animal, the method comprising: topically co-administering to the animal a mobile insect growth regulator component comprising methoprene or hydroprene, which is capable of translocating from one area to another area by vaporizing and redepositing, and a non-mobile insect growth regulator component comprising pyriproxyfen; wherein the amount of methoprene or hydroprene is between 0.01% and 10% by weight of the total formulation and the amount of pyriproxyfen is between 0.005% and 5% by weight of the total formulation.

2. The method of claim 1, wherein the mobile insect growth regulator component comprises methoprene.

3. The method of claim 1, wherein the mobile insect growth regulator component comprises hydroprene.

4. The method of claim 1, further comprising an adulticide, effective to kill adult parasites.

5. The method of claim 1, wherein a weight ratio of methoprene or hydroprene to pyriproxyfen is in the range of 20:1 to 1:20.

6. The method of claim 1, wherein the total formulation comprises 1% to 99% by weight of a carrier.

7. The method of claim 6, wherein the carrier is an N,N dialkyl fatty acid amide.

8. The method of claim 6, wherein the carrier is N,N dimethyl octanamide.

9. The method of claim 6, wherein the carrier is diisopropyl adipate (DIPA).

10. The method of claim 1, wherein the formulation comprises n-octyl pyrrolidone.

11. The method of claim 1, wherein the mobile insect growth regulator component and the non-mobile insect growth regulator component are applied to the animal in a single combined formulation.

12. The method of claim 1, wherein the mobile insect growth regulator component and the non-mobile insect growth regulator component are separated to prevent mixing prior to administration, and are dispensed simultaneously or nearly simultaneously onto the animal.

13. The method of claim 1, further comprising applying the mobile insect growth regulator component and the non-mobile insect growth regulator component to a surface in the animal's surroundings.

* * * * *